United States Patent
Liprie et al.

(10) Patent No.: US 6,491,662 B1
(45) Date of Patent: Dec. 10, 2002

(54) CATHETER WITH STAND-OFF STRUCTURE

(75) Inventors: Samuel F. Liprie, Lake Charles, LA (US); Lisa D. Futato, Milford, CT (US); Kenneth E. Toso; Gregory F. Toso, both of Wilton, CT (US)

(73) Assignee: Interventional Therapies LLC, Westport, CT (US)

(*) Notice: Subject to any disclaimer, the term of this patent is extended or adjusted under 35 U.S.C. 154(b) by 0 days.

(21) Appl. No.: 09/509,254

(22) PCT Filed: Sep. 23, 1998

(86) PCT No.: PCT/US98/19974
§ 371 (c)(1),
(2), (4) Date: Mar. 23, 2000

(87) PCT Pub. No.: WO99/15225
PCT Pub. Date: Apr. 1, 1999

Related U.S. Application Data
(60) Provisional application No. 60/060,693, filed on Sep. 23, 1997.

(51) Int. Cl.[7] ............................................. A61M 29/00
(52) U.S. Cl. .................................................... 604/97.01
(58) Field of Search .................... 604/96.01, 101.01, 604/97.01, 101.02–101.05, 102.01–102.03, 103.04, 915–921, 103.09, 264; 606/191–194

(56) References Cited

U.S. PATENT DOCUMENTS

| | | | | |
|---|---|---|---|---|
| 5,713,854 A | * | 2/1998 | Inderbitzen | 604/53 |
| 5,868,706 A | * | 2/1999 | Cox | 604/96 |
| 5,921,958 A | * | 7/1999 | Ressemann et al. | 604/96 |

* cited by examiner

*Primary Examiner*—Manuel Mendez
(74) *Attorney, Agent, or Firm*—Cantor Colburn LLP

(57) ABSTRACT

A catheter (10), and a method for performing radiation treatment at a site where angio-plasty was performed, are disclosed. The catheter (10) includes a hollow, cylindrical member (12) constructed from a fairly flexible material. The catheter is maneuvered within the body by traveling over a guide wire which was initially maneuvered in the blood vessel to a position beyond the actual site of a stenosis. Stand-off structure (26) having a stand-off balloon (28) surrounds a portion (30) of the outer surface of the catheter (10). The distal end (18) of the catheter (10) includes an inner lumen plug (38), and a distal mandrel (40) extending through the inner lumen plug (38). The distal mandrel (40) is manufactured from shape memory alloy to stiffen, and reinforce the catheter when the catheter is introduced within the blood vessel.

54 Claims, 9 Drawing Sheets

CATHETER WITH STAND-OFF STRUCTURE

PRIORITY

This application claims priority to PCT/US98/19974 which claims priority to a Provisional Application filed on Sep. 23, 1997 having Provisional Serial No. 60/060,693, the contents of which are incorporated herein by reference.

BACKGROUND

1. Technical Field

The present disclosure relates to intravascular catheters used for treating a stenosis in various blood vessels and other bodily conduits with radiation to inhibit restenosis, e.g., after angioplasty or other cardiovascular procedures, and particularly to an intravascular catheter reinforced with at least one stiffening mandrel to improve the pushability and maneuverability of the catheter as it moves through the circulatory system.

2. Background of the Related Art

Various techniques have been developed to treat many different conduits in the body when these conduits have become reduced in size due to the existence of a stenosis or have been completely occluded. These techniques include introducing a deflated balloon catheter to the site of the stenosis or occlusion, inflating the balloon one or more times to reduce the size of the stenosis, deflating the balloon and then removing the balloon catheter from the treatment site.

With respect to the vascular pathways, angioplasty is routinely used to open an artery or blood vessel in the region where the stenosis or the occlusion has occurred. A typical angioplasty procedure consists of making a small incision through the body and into a blood vessel and then maneuvering a guidewire through the vascular system to a point beyond the stenosis or occlusion. A hollow catheter with a deflatable balloon near its distal end is threaded over the guidewire and advanced to the point of stenosis or occlusion. The balloon is then inflated and deflated several times to widen the constricted area, and is then withdrawn from the body.

Unfortunately, although the angioplasty procedure does markedly reduce the area of stenosis or occlusion, many patients exhibit a reoccurrence of the stenosis within a few months of the original procedure. Although the original stenosis occurs by means of the build up of plaque over a relatively long period of time, studies have led many to believe that the reoccurrence of the stenosis after the original angioplasty procedure is unrelated to the cause of the original stenosis. It is believed that the inflation of the balloon catheter used in the angioplasty procedure or the placement of a stent in the area of the stenosis causes irritation to the blood vessel. This irritation produces a mechanism of action called hyperplasia, inducing the inner layer of the blood vessel cells to rapidly reproduce, thereby causing restenosis. It has been discovered that if the blood vessel is irradiated at the point of the stenosis with a radioactive dose immediately following the angioplasty procedure, the mechanism that causes hyperplasia would be inhibited without harming the blood vessel itself.

Accordingly, following the angioplasty procedure, the guide wire is typically left within the patient and an intravascular catheter is introduced over the guide wire. The intravascular catheter is pushed and maneuvered through the circulatory system until a distal end of the catheter is in proximity to the site of the angioplasty procedure. A source wire having at least one radioactive dose at a distal end is then advanced through the interior of the intravascular catheter until the distal end reaches the site of the angioplasty procedure. The radioactive dose is then left inside the catheter for a specific period of time to treat the area of the original stenosis.

It is often difficult to maneuver the intravascular catheter within the circulatory system, especially within narrow blood vessels such as the coronary arteries. To aid in steering and maneuvering the intravascular catheter through the circulatory system, a need exists to stiffen at least a portion of the intravascular catheter for allowing the intravascular catheter to be maneuvered through the circulatory system without crimping.

Additionally, during the radiation procedure, it is important to precisely control the amount of radiation which is directed to the blood vessel wall, since too much radiation could cause tissue damage while too little radiation could fail to inhibit hyperplasia. Therefore, a further need exists for properly positioning the radioactive dose within the blood vessel to address these issues.

SUMMARY

The present disclosure is directed to a catheter and a method for performing radiation treatment at a site where angioplasty was performed. The catheter includes a hollow, cylindrical member constructed from a fairly flexible material. The catheter is maneuvered within the body by traveling over a guidewire which was initially maneuvered in the blood vessel to a position beyond the actual site of a stenosis. The catheter is slightly tapered at its distal end to facilitate movement through blood vessels or similar conduits or ducts. Stand-off structure having a stand-off balloon surrounds a portion of the outer surface of the catheter.

The distal end of the catheter includes an inner lumen plug and a distal mandrel extending through the inner lumen plug. The distal mandrel is manufactured from shape memory alloy, such as a nickel-titanium alloy, to stiffen and reinforce the catheter when the catheter is introduced within the blood vessel. This adds strength to the distal end of the catheter which prevents the distal end of the catheter from crimping as the catheter is pushed and maneuvered through the circulatory system.

The stand-off balloon when inflated is preferably smaller in circumference than the circumference of the blood vessel, such that the inflated balloon is bumped-off from the inner surface of the blood vessel to provide some space between the inflated balloon and the blood vessel. This would allow blood to profuse through the space during the radiation treatment.

The method of the present disclosure entails that once the site of a stenosis is determined by appropriate diagnostic procedures and angioplasty is performed, the catheter with the stand-off balloon being deflated is threaded over the guidewire and is advanced such that the stand-off structure is maneuvered to the area where angioplasty was performed. The distal mandrel can also be used in conjunction with a longer fixed or removable stiffening mandrel for assisting in the maneuverability and positioning of the catheter within the circulatory system.

Once the stand-off balloon is verified to be in position, the stand-off balloon is inflated and kept inflated to bump-off the catheter from the walls of the vessel. One or more radioactive sources are provided on, or inside the distal end of a flexible source wire which is advanced through the interior of the cylindrical member of the catheter until it reaches the proper location. The radioactive source is then left inside the catheter for a specific period of time to treat the area of the original stenosis.

BRIEF DESCRIPTION OF THE DRAWINGS

Various preferred embodiments are described herein with references to the drawings.

DETAILED DESCRIPTION OF PREFERRED EMBODIMENTS

Although the catheter disclosed herein can be used to provide radiation treatment to many body conduits following angioplasty or other cardiovascular procedures, for ease of explanation, the catheter will be discussed with respect to providing radiation treatment to a blood vessel, such as a coronary artery, for a specified period of time to prevent reclosure or restenosis of the vessel due to hyperplasia or smooth muscle cell proliferation.

Figure 1:
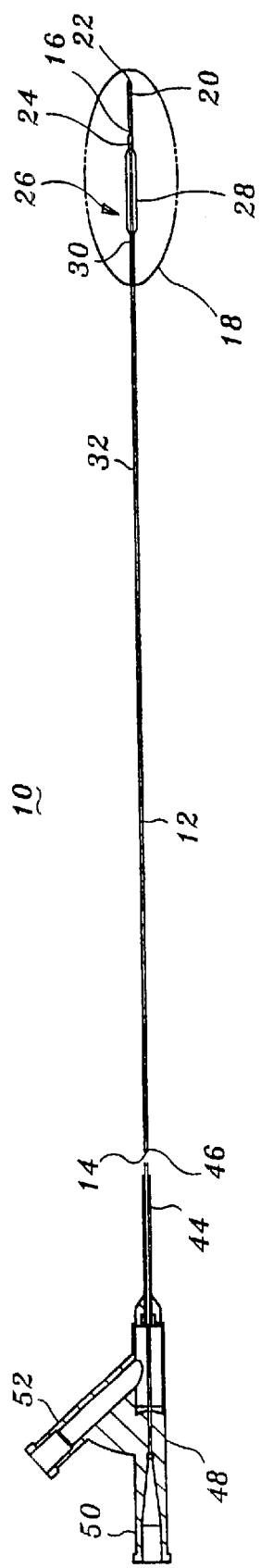
FIG. 1 is a side cross-sectional view of a catheter having stand-off structure according to a first embodiment of the present disclosure.

FIG. 1 is a side cross-sectional view of the catheter of the present disclosure designated generally by reference numeral 10. The catheter itself consists of a hollow, generally cylindrical member 12 which is constructed from a fairly flexible material such as polyethylene glycol so that it can be easily maneuvered within the body and travel over a guidewire which was initially maneuvered in the blood vessel to a position beyond the actual site of the stenosis. The interior 14 of cylindrical member 12 can be made of or coated with a friction reducing material such as polytetrafluoroethylene to aid in the passing of a radioactive source wire to the treatment site.

Figure 2:
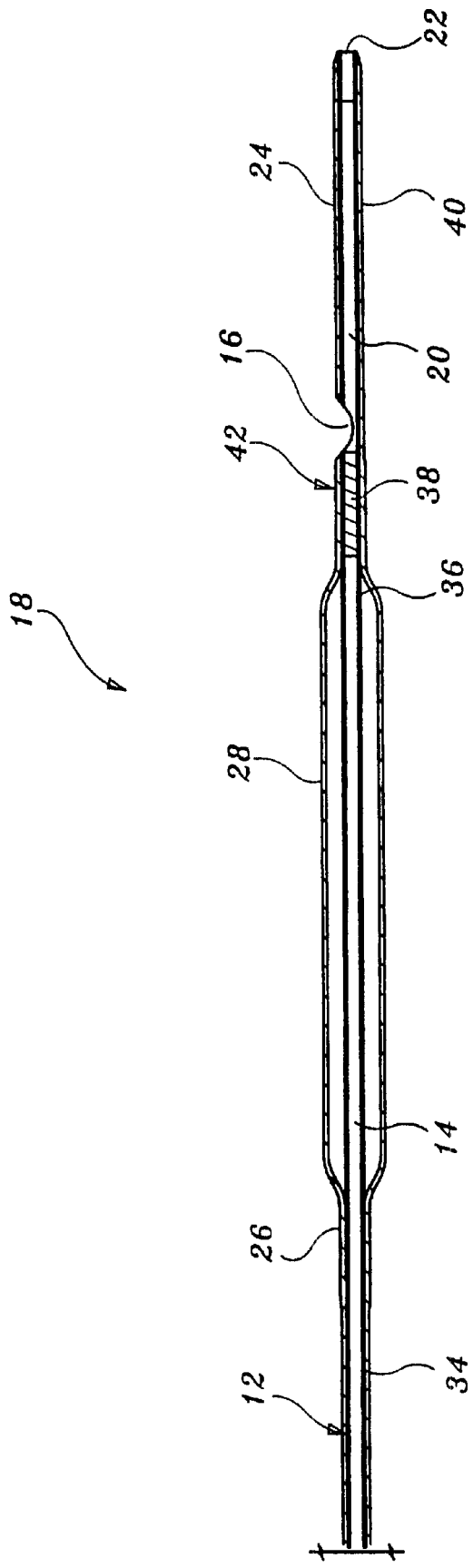
FIG. 2 is an enlarged view of the distal end of the catheter shown by FIG. 1.

Referring to FIGS. 1 and 2, catheter 10 has a notch 16 at a distal end 18, of catheter 10, which is in open communication with a bore 20 extending from cylindrical member 12. Bore 20 leads to an opening 22 from which the guidewire can exit cylindrical member 12 for guiding catheter 10 to the proper location within the blood vessel. The exterior of cylindrical member 12 over bore 20 includes a tip jacket 24 manufactured from low-density polyethylene.

Catheter 10 is approximately 120 cm in length and is slightly tapered at its distal end 18 to facilitate movement through blood vessels or similar conduits or ducts. Both the guidewire and catheter 10 should be of sufficient length to travel to the site where angioplasty was performed. Stand-off structure 26 having a stand-off balloon 28 surrounds a portion 30 of the outer surface of catheter 10. Stand-off balloon 28 is approximately 20 mm in length and in embodiments described hereinbelow preferably contains a number of pleats or lobes. Stand-off balloon 28 is preferably manufactured from low-density polyethylene. The portion of cylindrical member 12 disposed within stand-off structure 26 is preferably manufactured from high-density polyethylene and may include one or more ports (not shown) to provide fluid communication between the interior 14 of cylindrical member 12 and stand-off balloon 28.

As shown by FIG. 2, catheter 10 includes two radiopaque markers 34 and 36 which are approximately 90% platinum and 10% iridium. Markers 34 and 36 are preferably 3 cm apart from each other and are located underneath stand-off structure 26. Distal end 18 of catheter 10 further includes an inner lumen plug 38 and a distal mandrel 40 extending through inner lumen plug 38 to the distal end of cylindrical member 12. Inner lumen plug 38 is preferably manufactured from low-density polyethylene.

Distal mandrel 40 is manufactured from a shape memory alloy, such as a nickel-titanium alloy, to stiffen catheter 10 when catheter 10 is introduced within the blood vessel. This prevents distal end 18 of catheter 10 from crimping as catheter 10 is pushed and maneuvered through the circulatory system. Distal mandrel 40 is sufficiently parallel to bore 20 to also provide support to the portion of cylindrical member 12 surrounding bore 20. It is preferred that catheter 10 is maneuvered in a manner designed to keep distal mandrel 40 sufficiently parallel to the blood vessel.

It is contemplated that distal mandrel 40 extend proximally beyond inner lumen plug 38 to stiffen a major portion of catheter 10. It is further contemplated that distal mandrel 40 has a distal portion having smaller transverse dimensions than a proximal portion. Preferred transverse dimensions for distal mandrel 40 are approximately 0.0085–0.0095 inches for the proximal end and 0.0035–0.0045 inches for the distal end. It is further preferred that the length of distal mandrel 40 is approximately 0.587 to 0.987 inches.

In addition, it is further contemplated that more than one distal mandrel 40 is connected to the distal end of cylindrical member 12. It is also contemplated that distal mandrel 40 is cylindrical in shape and encases the distal end of cylindrical member 12.

Since the catheter of the present disclosure can act as a conduit to allow a reusable radiation source to be introduced to the site of the original stenosis, cylindrical member 12 is sealed at a point proximate to its distal end 18, while allowing a guidewire to exit distal end 18. Therefore, stand-off structure 26, tip jacket 24, and distal mandrel 40 are joined or bonded together, e.g., by melting or welding, to form a bonded distal tip 42 as shown in FIG. 2 to seal catheter 10 at a point proximate to its distal end 18 while allowing the guidewire to exit distal end 18 of catheter 10 through bore 20 (or notch 16). It is noted that during the process of bonding to form bonded distal tip 42 the inner lumen plug 38 is formed as well.

Bonded distal tip 42 effectively seals hollow, cylindrical member 12 of catheter 10 to prevent any blood or contaminants from entering interior 14 of cylindrical member 12 to keep interior 14 sterile. This is necessary since blood and contaminants within cylindrical member 12 can inhibit the proper placement of the radioactive source and contaminate the reusable radioactive source.

Catheter 10 further includes a strain relief member 44 at a proximal end 46 of cylindrical member 12 to provide flexibility as cylindrical member 12 is inserted within a blood vessel (FIG. 1). Strain relief member 44 is preferably manufactured from low-density polyethylene. A portion of strain relief member 44 and proximal end 46 of cylindrical member 12 are inserted within a luer hub 48 and preferably chemically adhered to luer hub 48 by an adhesive. Luer hub 48 includes a funnel port 50 in alignment with interior 14 of cylindrical member 12 and an inflation port 52.

Figure 3:
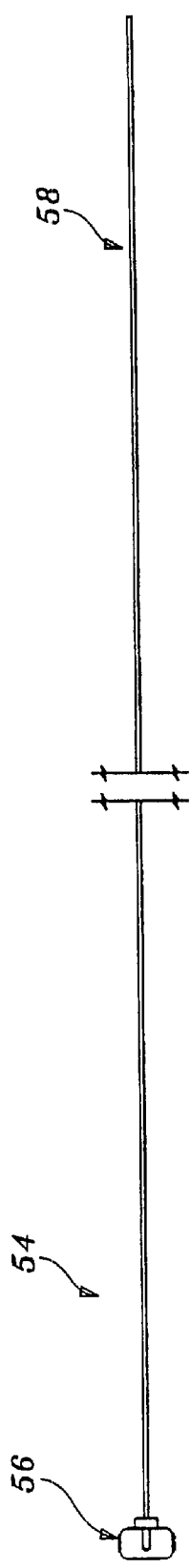
FIG. 3 is a side view of a stiffening mandrel which is inserted within the catheter having stand-off structure of FIG. 1.

Funnel port 50 allows for the introduction of a removable stiffening mandrel 54 as shown by FIG. 3 having a luer cap 56 through interior 14 of cylindrical member 12. Stiffening mandrel 54 is slightly tapered at its distal end 58 and is manufactured from a shape memory alloy, such as a nickel-titanium alloy [nitinol]. Luer cap 56 is preferably manufactured from lexan and a polycarbonate.

Stiffening mandrel 54 extends through interior 14 of cylindrical member 12 to provide pushability and strength to catheter 10 as it is guided over a guidewire for allowing catheter 10 to be maneuvered through the circulatory system without crimping. When stand-off structure 26 of catheter 10 reaches the site of the original stenosis, stiffening mandrel 54 is removed from catheter 10. Fluid, preferably saline or a fluoroscopically visible saline mixture, is then introduced within cylindrical member 12 through inflation port 52 into an inflation lumen (not shown) which is concentric to interior 14 to inflate stand-off balloon 28 and properly position catheter 10 within the blood vessel for introducing the radioactive source to the original site of the stenosis. Such inflation lumen construction is known in over-the-wire type catheters; an example of a concentric inflation lumen is illustrated with respect to the embodiment shown in at least FIG. 7 hereinbelow.

It is contemplated that stiffening mandrel 54 may be permanently fixed within a bore in catheter 10. It is further contemplated that stiffening mandrel 54 is integral with distal mandrel 40.

It is preferred for stand-off balloon 28 when inflated to be smaller in circumference than the circumference of the blood vessel, such that the inflated balloon is bumped-off from the inner surface of the blood vessel to provide some space between the inflated balloon and the blood vessel. This would allow blood to profuse through the space during the radiation treatment. This flow of blood would greatly decrease the incidence of a myocardial infarction or a heart attack and would allow the radiation treatment to be performed as long as needed without completely blocking the flow of blood through the blood vessel.

Figure 4:
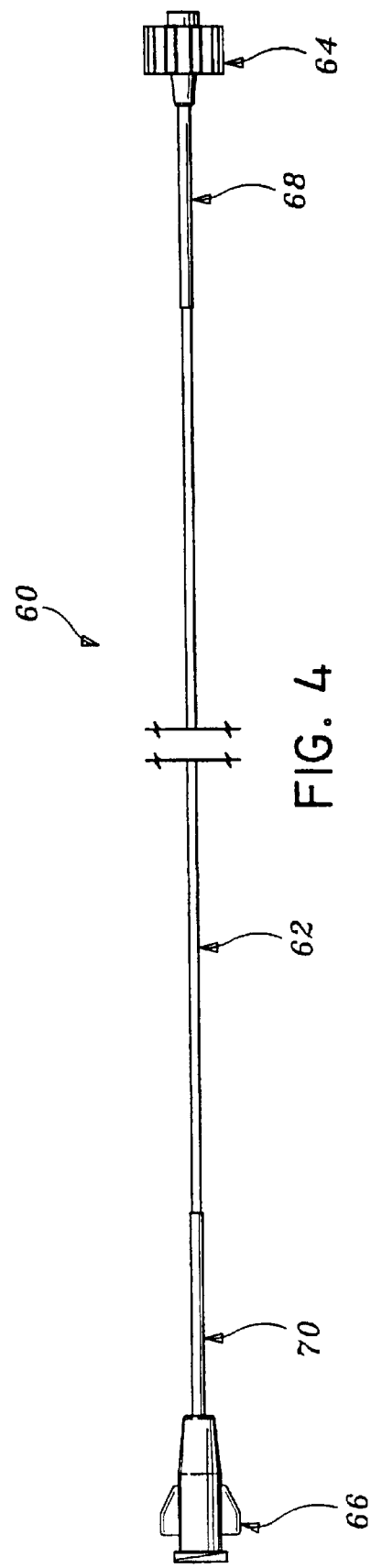
FIG. 4 is a side view of an extension catheter which is connected at the proximal end of the catheter shown by FIG. 1.
Figure 5:
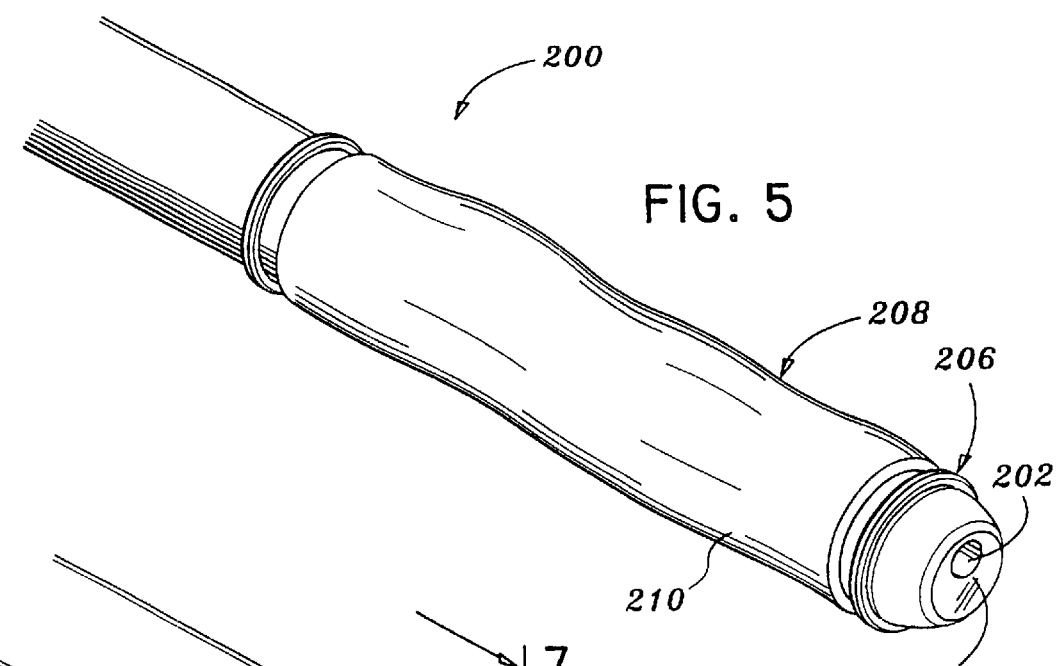
FIG. 5 is a perspective view of stand-off structure of a catheter of a second embodiment with the stand-off balloon being deflated.
Figure 6:
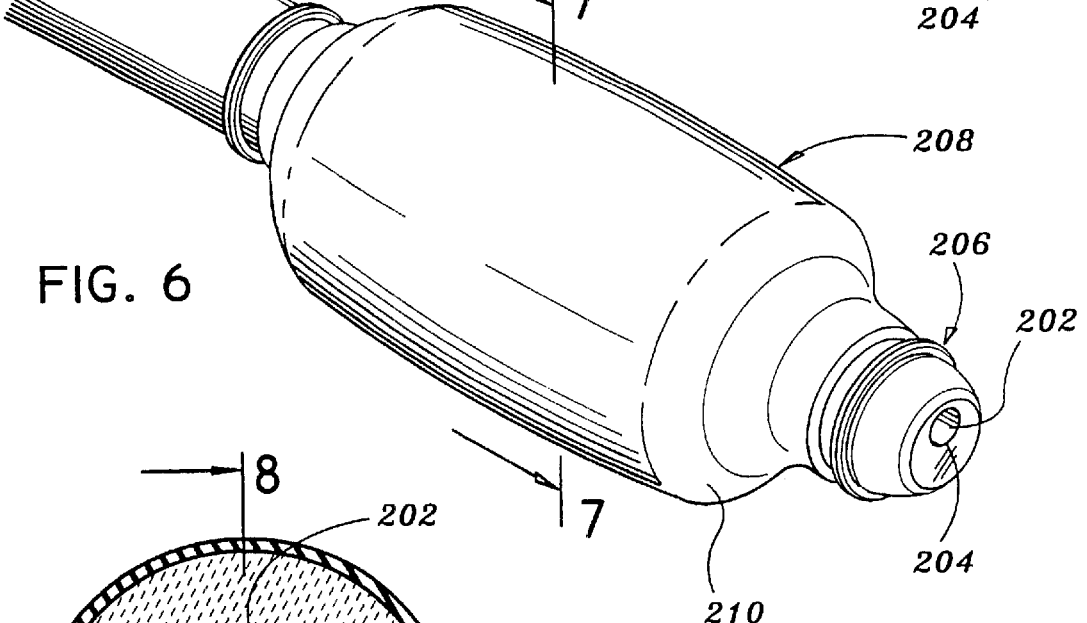
FIG. 6 is a perspective view of the stand-off balloon of the catheter embodiment shown by FIG. 5 being inflated.

With reference to FIG. 4, a catheter extension is shown, designated generally by reference numeral 60, having a clear cylindrical rube 62 manufactured from polyethylene to enable the source wire introduced therein to be visualized. Catheter extension 60 includes a male adaptor 64 configured to matingly engage funnel port 50 of luer hub 48. Catheter extension 60 further includes a female adaptor 66, at an end opposite male adaptor 64, for connection to a source wire container, such as an afterloader. Strain relief members 68 and 70 are provided proximate the male and female adaptors 64 and 66, respectively, and are preferably manufactured from low-density polyethylene. The source wire is introduced through female adaptor 66 and is guided through luer hub 48 and interior 14 of cylindrical member 12.

The stand-off balloon catheter as described herein can be utilized in the following manner to prevent reoccurrence of the stenosis. Once the site of a stenosis is determined ba appropriate diagnostic procedures and angioplasty is performed, catheter 10 with stand-off balloon 28 being deflated is threaded over the guidewire and is advanced such that stand-off structure 26 is maneuvered to the area where angioplasty was performed. Radiopaque markers 34 and 36 on both ends of stand-off structure 26 allow catheter 10 to be imaged under fluoroscopy. Once stand-off balloon 28 is verified to be in position, stand-off balloon 28 is inflated and kept inflated to bump-off catheter 10 from the walls of the vessel.

One or more radioactive sources are provided on, or inside the distal end of a flexible source wire which is advanced through interior 14 of cylindrical member 12 of catheter 10 until it reaches the proper location. The radioactive source is then left inside catheter 10 for a specific period of time to treat the area of the original stenosis. The time the source remains inside catheter 10 depends upon the strength of the radioactive source and the distance between the source and the inner blood vessel walls. Examples of radiation sources which can be utilized in this procedure would be cesium 137, cobalt 60, iodine 125, iodine 131, cobalt 57, iridium 192, gold 198, palladium 103. strontium 89, strontium 90, yttrium 90, phosphorus 32, etc. Typically, treatment times could last between approximately four minutes to approximately thirty minutes or longer. Since iridium 192 has a well-defined energy level with a strength of 1–2 Curies, it is particularly well-suited to treat the area of the original stenosis at the prescribed distance. In this instance, treatment times would be in the range of 5 to 10 minutes. After the radiation treatment has been completed, the source wire and radiation source are removed followed by the catheter 10, with the balloon deflated.

With reference to FIGS. 5–13, additional embodiments of catheters having stand-off structures are illustrated and are to be used in the same manner as discussed above for catheter 10 in preventing restenosis at an area within a blood vessel where angioplasty was performed. It is contemplated that the following additional embodiments are manufactured from the same materials used to manufacture catheter 10 and that they can include a distal mandrel.

FIGS. 5–8 illustrate a second embodiment of a catheter having stand-off structure designated generally by reference numeral 200. Catheter 200 is an over-the wire type catheter since the guidewire traverses within the entire length of cylindrical member 202 and extends through opening 204 at distal end 206 of catheter 200. Catheter 200 includes stand-off structure 208 in the form of a stand-off balloon 210 which can be deflated (FIG. 5) or inflated (FIG. 6) through an inflation lumen 209.

Figure 7:
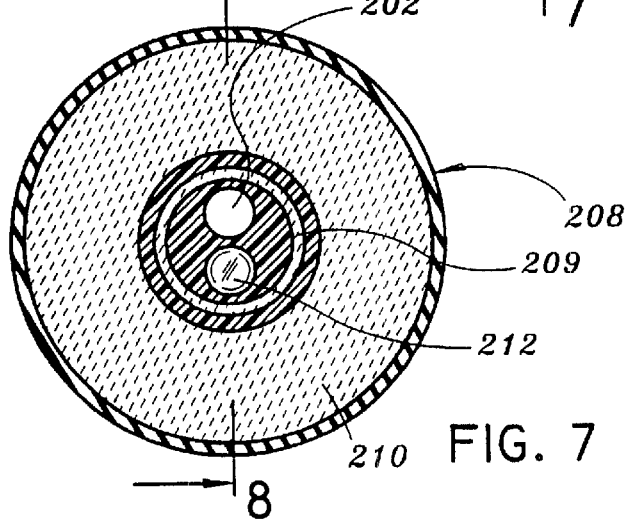
FIG. 7 is a cross-sectional view taken along line 7—7 in FIG. 6.
Figure 8:
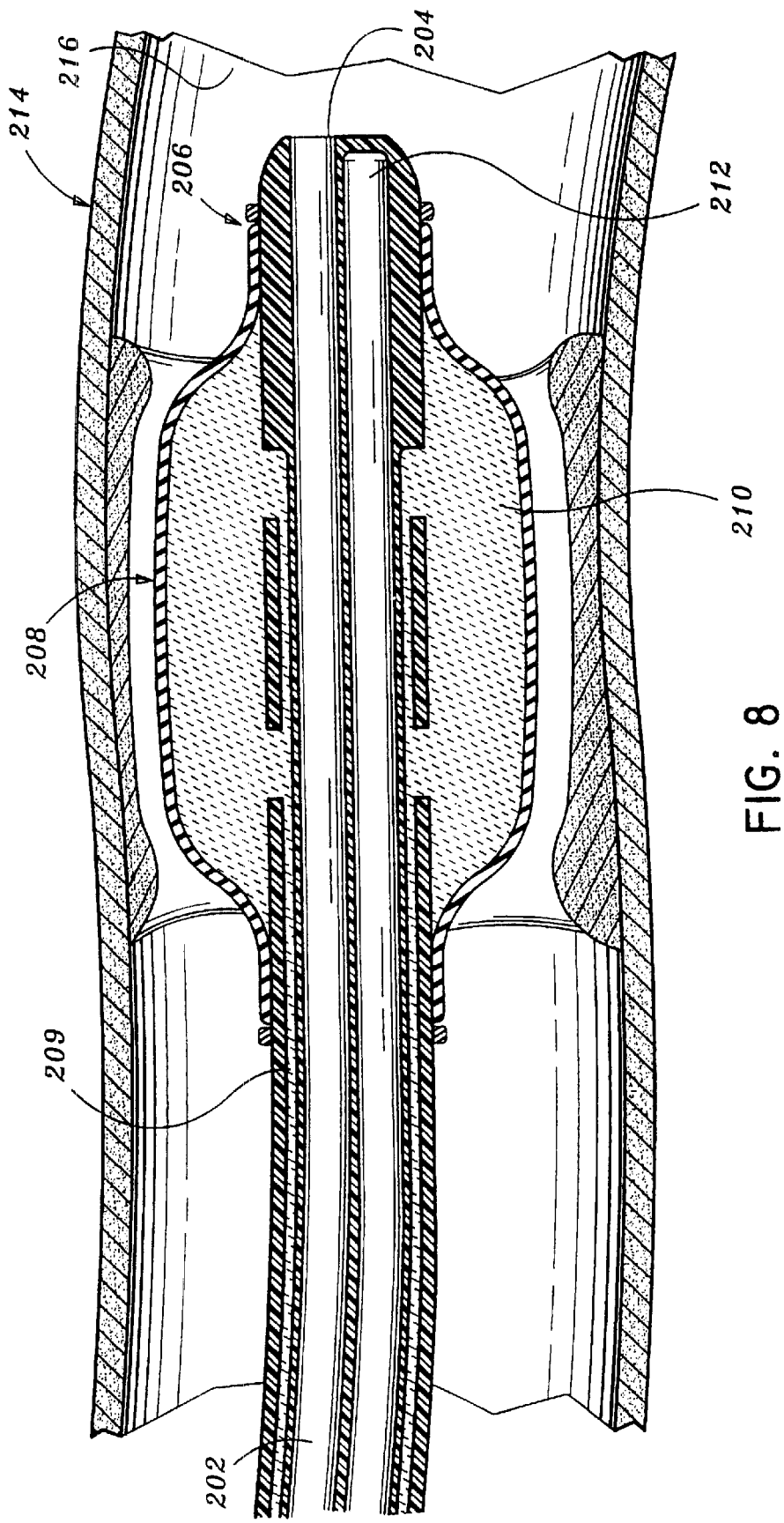
FIG. 8 is a side cross-sectional view of the catheter embodiment shown by FIG. 5 within a blood vessel.

As shown by FIG. 7, when stand-off balloon 210 is inflated it is substantially circular is shape. Further, as shown by FIG. 7, there is a second cylindrical member 212 which extends substantially the length of catheter 200 for receiving a source wire therein having a radioactive source at a distal end. Cylindrical member 212 is sealed at its distalmost end to prevent blood and contaminants from entering therein. FIG. 8 illustrates catheter 200 within a blood vessel 214 depicting stand-off balloon 210 inflated and bumped-off from side walls 216 of vessel 214 to position cylindrical member 212 away from side walls 216.

Figure 9:
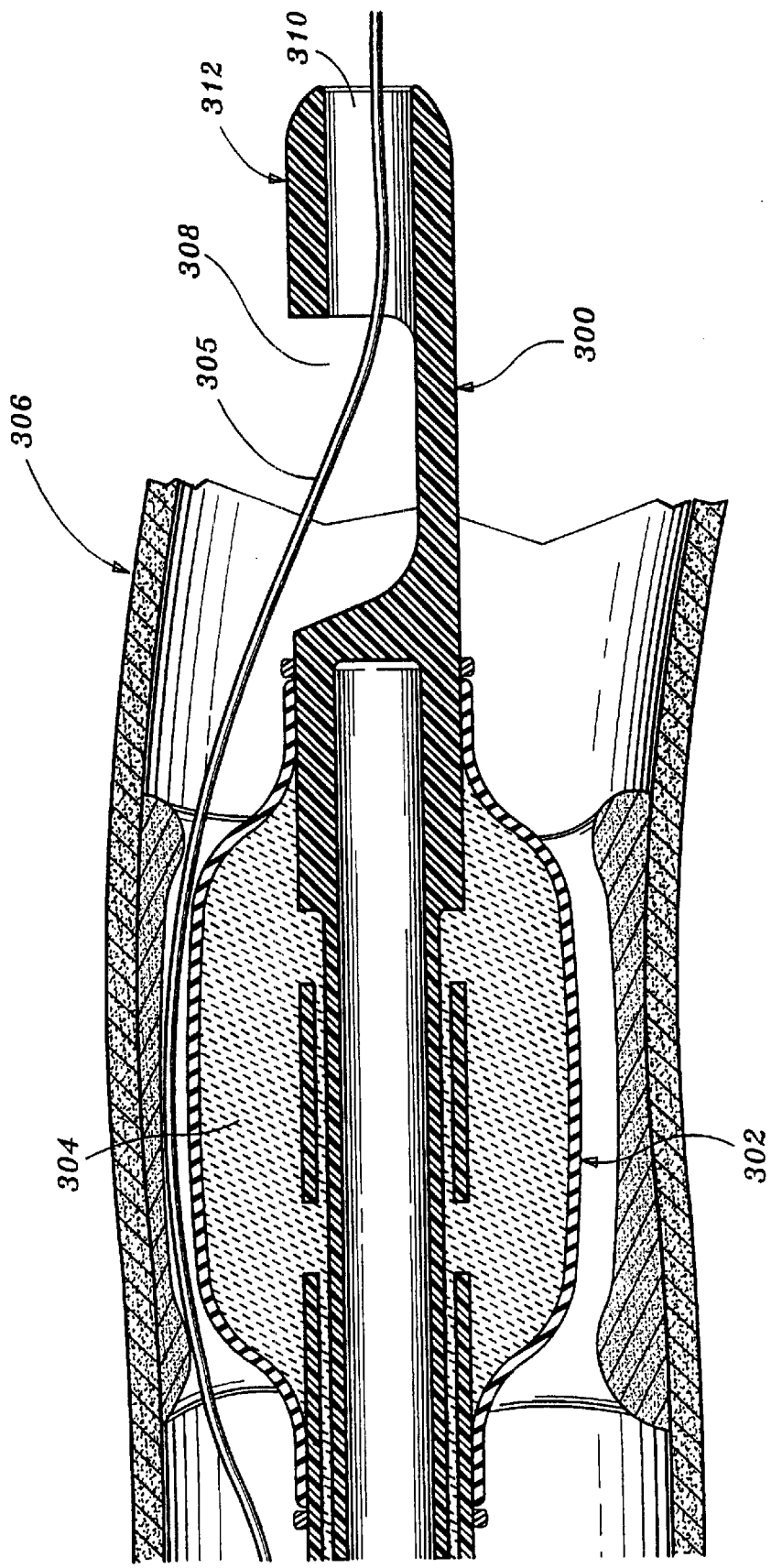
FIG. 9 is a side cross-sectional view of the distal end of a catheter of a third embodiment within a blood vessel.

FIG. 9 illustrates a third embodiment of a catheter designated generally by reference numeral 300. Catheter 300 has stand-off structure 302 which includes a stand-off balloon 304. FIG. 9 illustrates the passage of guidewire 305 through blood vessel 306 and through a notch 308 and bore 310 at distal end 312 of catheter 300. Catheter 300 also includes a cylindrical member 314 for receipt of a source wire and an inflation lumen 316 concentric with cylindrical member 314.

Figure 10:
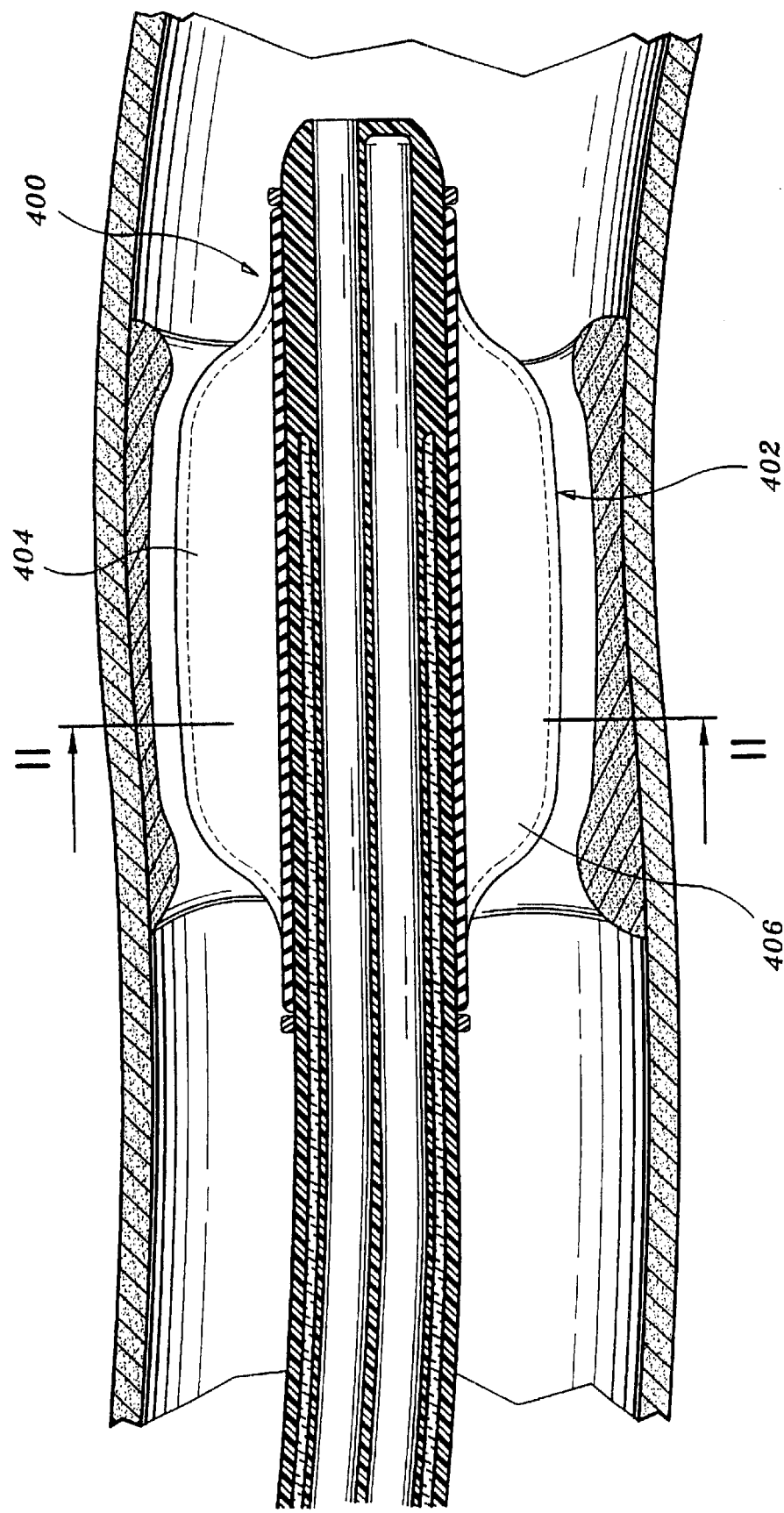
FIG. 10 is a side cross-sectional view of the distal end of a catheter of a fourth embodiment within a blood vessel.
Figure 11:
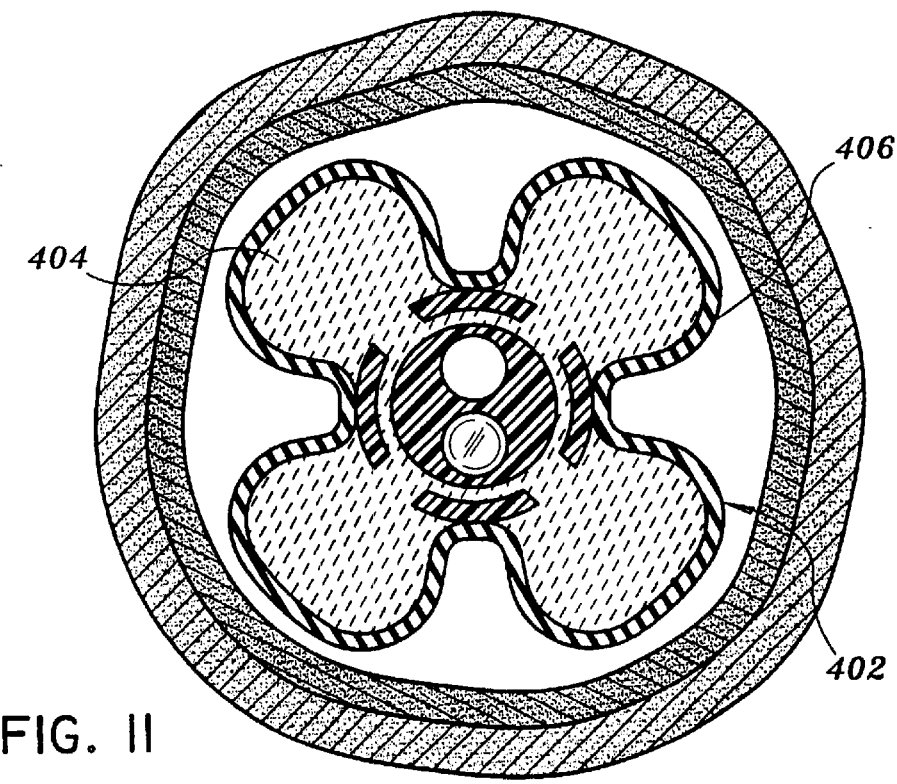
FIG. 11 is a cross-sectional view taken along line 11—11 in FIG. 10.

FIG. 10 illustrates a fourth embodiment of a catheter designated generally by reference numeral 400. Catheter 400 is similar to the second embodiment but contains stand-off structure 402 having a stand-off balloon 404 which has four lobes 406, as shown by FIG. 11, to allow blood to profuse between lobes 406 when balloon 404 is inflated. Catheter 400 also includes a cylindrical member 414 for receipt of a guidewire, a source wire lumen 416 for receipt of a source wire having a radioactive source, and an inflation lumen 418.

Figure 13:
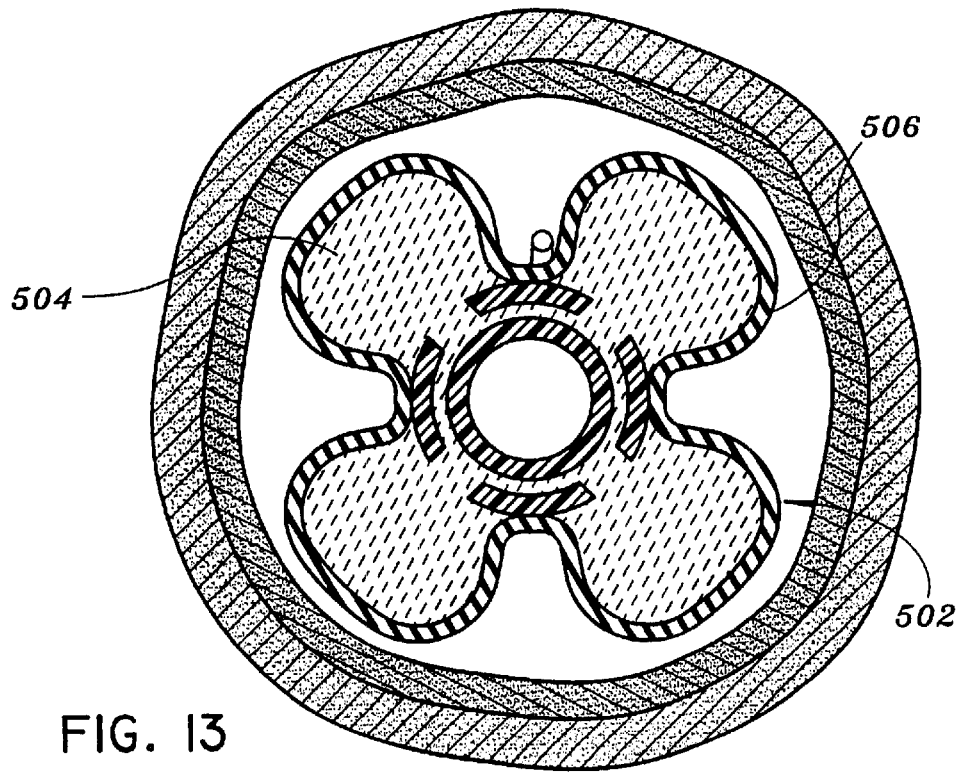
FIG. 13 is a cross-sectional view taken along line 13—13 in FIG. 12.
Figure 12:
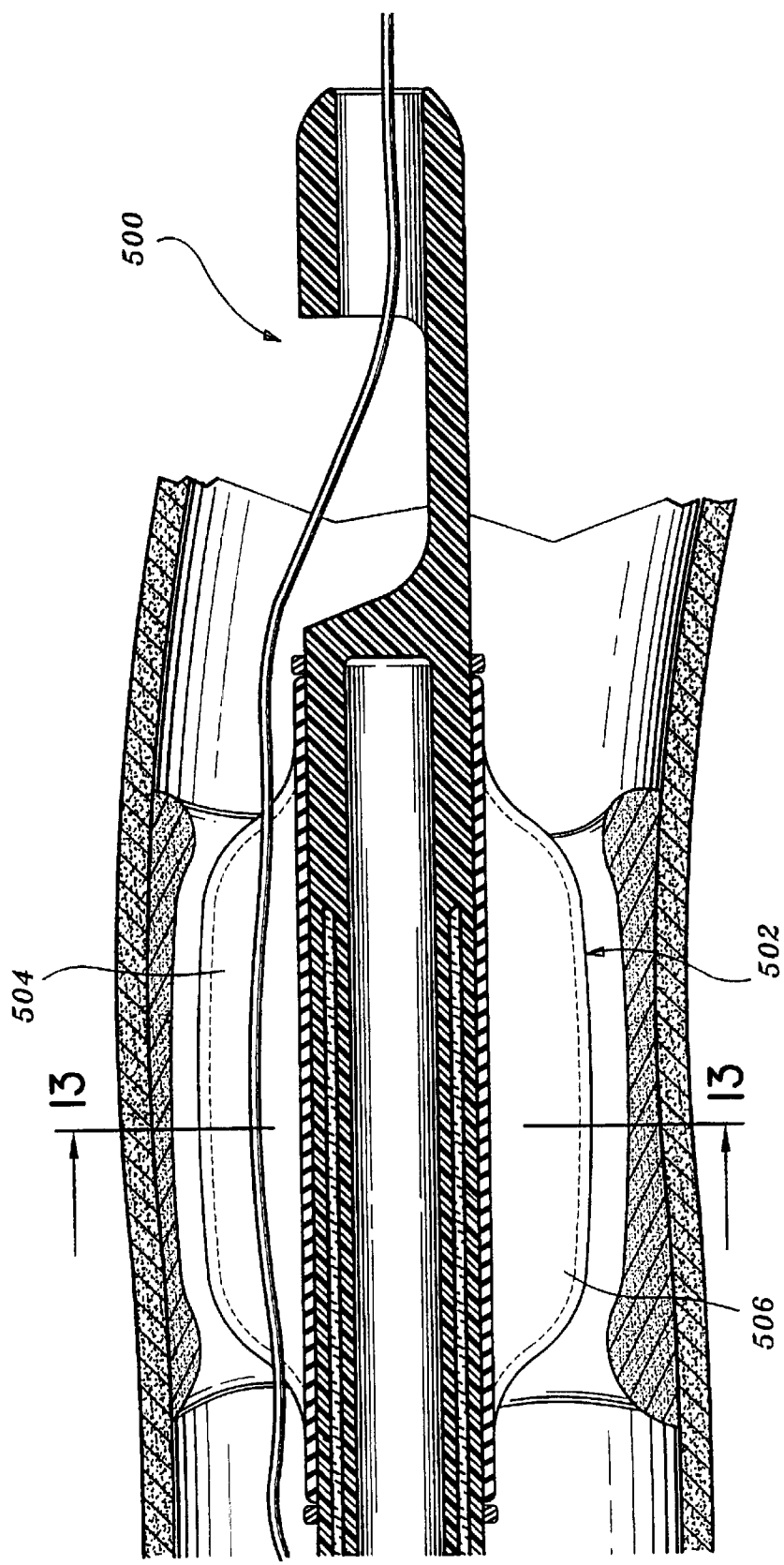
FIG. 12 is a side cross-sectional view of the distal end of a catheter of a fifth embodiment within a blood vessel.

FIGS. 12–13 illustrate a fifth embodiment of a catheter designated generally by reference numeral 500. Catheter 500 is similar to the third embodiment but contains stand-off structure 502 having a stand-off balloon 504 which has four lobes 506, as shown by FIG. 13. to allow blood to profuse between lobes 506 when balloon 504 is inflated. Catheter 500 also includes a cylindrical member 514 for receipt of a source wire and an inflation lumen 516 concentric with cylindrical member 514.

Although the embodiments herein have been explained with respect to an angioplasty procedure, it can also be used to treat cancer in various areas of the body, such as the common bile duct, the bladder, the liver, the lungs, etc. employing the same balloon catheters with stand-off structures shown in the figures. Those skilled in the art will envision other modifications within the scope and spirit of the claims appended hereto.

What is claimed:

1. A catheter system, comprising:
   a catheter having a cylindrical member which includes a proximal end and a distal end, the cylindrical member further having at least one passageway extending from the proximal end to a distal end portion;
   a stand-off structure having a stand-off balloon surrounding a portion of the distal end portion, the stand-off balloon being in fluid communication with a portion of at least one passageway;
   a luer hub connected to the proximal end of the cylindrical member, the luer hub having a first port in fluid communication with the at least one passageway for delivering a substance to an interior chamber of the stand-off structure for inflating the stand-off balloon, the luer hub further having a second port in alignment with a first bore extending from the proximal end to the distal end portion of the cylindrical member, wherein the first bore is sealed at a point proximate to the distal end portion of the cylindrical member;
   a stiffening mandrel configured for introduction through the second port, the stiffening mandrel extending through the first bore within the cylindrical member for maneuvering the cylindrical member through the circulatory system; and
   a distal mandrel extending distally from the stand-off structure for stiffening the distal end of the cylindrical member.

2. The catheter system according to claim 1, wherein the distal mandrel extends through an inner lumen plug which forms a seal at a distal end of the first bore.

3. The catheter system according to claim 1, wherein the distal mandrel is manufactured from a shape memory alloy.

4. The catheter system according to claim 1, wherein the stiffening mandrel has a tapered distal end.

5. The catheter system according to claim 4, wherein the stiffening mandrel is manufactured from a shape memory alloy.

6. The catheter system according to claim 1, further including a catheter extension having a cylindrical member including a central bore in alignment with the first bore, the catheter extension further having a distal end configured to matingly engage the second port.

7. The catheter system according to claim 6, further including a source wire having at least one radiation source at a distal end, the source wire configured for traversing the central bore of the catheter extension and the first bore for delivering the at least one radiation source in proximity to the stand-off structure.

8. The catheter system according to claim 1, wherein the cylindrical member includes a second bore leading to an opening at a distal end of the cylindrical member.

9. The catheter system according to claim 8, wherein the catheter has a notch in fluid communication with the second bore for introducing a guidewire into the second bore.

10. The catheter system according to claim 9, wherein the notch is located distally from the stand-off structure.

11. The catheter system according to claim 1, wherein the catheter is approximately 120 cm in length.

12. The catheter system according to claim 1, wherein the stand-off structure is approximately 20 mm in length.

13. The catheter system according to claim 1, wherein an exterior portion of the catheter includes a tip jacket.

14. The catheter system according to claim 12, wherein the tip jacket is manufactured from polyethylene.

15. The catheter system according to claim 1, wherein the distal end of the cylindrical member is tapered.

16. The catheter system according to claim 1, wherein the catheter is manufactured from polyethylene glycol.

17. The catheter system according to claim 1, wherein an interior of the first bore is coated with polytetrafluoroethylene.

18. The catheter system according to claim 1, further comprising at least two radiopaque markers positioned on the distal end of the cylindrical member.

19. The catheter system according to claim 18, wherein the at least two radiopaque markers are positioned underneath the stand-off structure.

20. The catheter system according to claim 18, wherein the at least two radiopaque markers are approximately 90% platinum and 10% iridium.

21. The catheter system according to claim 1, wherein the stand-off structure and the distal mandrel are bonded together to form a bonded distal tip.

22. The catheter system according to claim 21, wherein the bonded distal tip forms a seal which seals the first bore of the cylindrical member.

23. The catheter system according to claim 1, wherein the catheter includes at least one strain relief member at the proximal end of the cylindrical member for providing flexibility to the cylindrical member.

24. The catheter system according to claim 1, wherein the stand-off balloon is dimensioned and configured to be smaller in diameter when inflated, than a target blood vessel the catheter is inserted in to create a space between an outer surface of the stand-off balloon and an inner surface of the blood vessel for allowing blood to profuse between the space.

25. The catheter system according to claim 6, wherein the cylindrical member of the catheter extension is transparent and manufactured from polyethylene.

26. The catheter system according to claim 6, wherein the catheter extension further includes a female adaptor at an end opposite the distal end, the female adaptor configured for connecting the catheter extension to a source wire container.

27. The catheter system according to claim 6, wherein the catheter extension further includes at least one strain relief member on the cylindrical member.

28. The catheter system according to claim 1, wherein the at least one passageway is concentric to the first bore.

29. The catheter system according to claim 7, wherein the at least one radiation source is selected from the group consisting of cesium 137, cobalt 60, iodine 125, iodine 131, cobalt 57, iridium 192, gold 198, palladium 103, strontium 89, strontium 90, yttrium 90 and phosphorus 32.

30. The catheter system according to claim 1, wherein the stand-off balloon has at least two lobes for allowing blood to profuse between the at least two lobes when the stand-off balloon is inflated.

31. A catheter adapted for traversing the circulatory system to provide radiation treatment to at least ore site within the circulatory system following a cardiovascular procedure, the catheter comprising:
  a cylindrical member having a proximal end and a distal end, the cylindrical member including a first and a second passageway extending from the proximal end to a distal end portion;
  a stand-off structure in proximity to the distal end portion of the cylindrical member having a stand-off balloon in fluid communication with the first passageway;
  an adaptor structure connected to the proximal end of the cylindrical member and including a first port in fluid communication with the first passageway and a second port in fluid communication with the second passageway, wherein the second passageway is configured for introducing therein a source wire having at least one radiation source at a distal end, the source wire configured for traversing the second passageway for delivering the at least one radiation source in proximity to the stand-off structure; and
  a distal mandrel positioned on the cylindrical member and extending beyond a distal end of the stand-off structure.

32. The catheter according to claim 31, wherein the cylindrical member includes a third passageway leading to an opening at the distal end of the cylindrical member.

33. The catheter according to claim 32, wherein the third passageway is configured for introducing therein a guidewire for guiding the catheter through the circulatory system.

34. The catheter according to claim 31, wherein the catheter is approximately 120 cm in length.

35. The catheter according to claim 31, wherein the stand-off structure is approximately 20 mm in length.

36. The catheter according to claim 31, wherein the distal end of the cylindrical member is tapered.

37. The catheter according to claim 31, wherein the catheter is manufactured from polyethylene glycol.

38. The catheter according to claim 31, further comprising at least two radiopaque markers positioned on distal end of the cylindrical member.

39. The catheter according to claim 31, wherein the distal mandrel extends through an inner lumen plug configured to seal the second passageway.

40. The catheter according to claim 31, wherein the distal mandrel is manufactured from a shape memory alloy.

41. The catheter according to claim 31, wherein the second passageway is sealed at a point proximate the distal end of the cylindrical member.

42. The catheter according to claim 31, wherein a distal portion of the stand-off structure and the distal mandrel are bonded together to form a bonded distal tip.

43. The catheter according to claim 42, wherein the bonded distal tip forms a seal which seals the second passageway of the cylindrical member.

44. The catheter according to claim 31, further comprising at least one strain relief member at the proximal end of the cylindrical member for providing flexibility to the cylindrical member.

45. The catheter according to claim 31, wherein the stand-off balloon is dimensioned and configured to be smaller in diameter when inflated than a target blood vessel the catheter is inserted in to create a space between an outer surface of the stand-off balloon and an inner surface of the blood vessel for allowing blood to profuse between the space.

46. The catheter according to claim 31, wherein the first and second passageways are concentric to each other.

47. The catheter according to claim 32, wherein the at least one radiation source is selected from the group consisting of cesium 137, cobalt 60, iodine 125, iodine 131, cobalt 57, iridium 192, gold 198, palladium 103, strontium 89, strontium 90, yttrium 90 and phosphorus 32.

48. The catheter according to claim 31, wherein the stand-off balloon has at least two lobes for allowing blood to profuse between the at least two lobes when the stand-off balloon is inflated.

49. The catheter according to claim 42, wherein the distal mandrel and the distal portion of the stand-off structure are bonded together by welding.

50. The catheter according to claim 31, wherein the distal mandrel has a distal portion having smaller transverse dimensions than a proximal portion of the distal mandrel.

51. The catheter according to claim 31, wherein the distal mandrel is cylindrical in shape and encased within the distal end of the cylindrical member.

52. A method for providing radiation treatment to a site within a body lumen to maintain the patency of the body lumen following a cardiovascular procedure at the site, the method comprising the steps of:
  providing a catheter having:
    a cylindrical member having a proximal end and a distal end, the cylindrical member including a first and a second passageway extending from the proximal end to the distal end, the cylindrical member further including a bore originating at a first opening and terminating at a second opening at the distal end of the cylindrical member;
    stand-off structure in proximity to the distal end of the cylindrical member having a stand-off balloon in fluid communication with the first passageway;
    an adaptor structure connected to the proximal end of the cylindrical member and including a first port in fluid communication with the first passageway and a second port in fluid communication with the second passageway; and
    a distal mandrel positioned on the cylindrical member and extending beyond a distal end of the stand-off structure for increasing the stiffness of the cylindrical member as it is guided along a guidewire;
  positioning the guidewire in the body lumen;
  advancing the catheter over the guidewire by inserting the guidewire in the bore through the second opening to traverse the bore and exit through the first opening;

advancing the cylindrical member over the guidewire by maneuvering the catheter to keep the distal mandrel sufficiently parallel to the body lumen until the stand-off structure is positioned at the site of the cardiovascular procedure;

providing a fluid within the first port to flow through the first passageway to inflate the stand-off balloon;

inserting a source wire having at least one radiation source at a distal end within the second passageway through the second port until the distal end of the source wire is in proximity to the stand-off structure;

deflating the stand-off balloon; and withdrawing the cylindrical member and the source wire from the body lumen.

53. The method for providing radiation treatment to a site within a body lumen according to claim 52, further comprising the step of inserting a stiffening mandrel within the second passageway through the second port during the step of advancing the cylindrical member over the guidewire.

54. The method for providing radiation treatment to a site within a body lumen according to claim 52, further comprising the step of removing the stiffening mandrel prior to the step of inserting the source wire.

\* \* \* \* \*